(12) United States Patent
Yan et al.

(10) Patent No.: US 10,967,099 B2
(45) Date of Patent: Apr. 6, 2021

(54) COMPOSITE BONE IMPLANT MATERIAL AND METHOD OF MAKING THEREOF

(71) Applicant: SICHUAN NATIONAL NANO TECHNOLOGY CO., LTD, Sichuan (CN)

(72) Inventors: Yonggang Yan, Sichuan (CN); Peng Wang, Sichuan (CN); Hong Li, Sichuan (CN); Fan Xu, Sichuan (CN); Pengzhen Liu, Sichuan (CN)

(73) Assignee: SICHUAN NATIONAL NANO TECHNOLOGY CO., LTD, Sichuan (CN)

( * ) Notice: Subject to any disclaimer, the term of this patent is extended or adjusted under 35 U.S.C. 154(b) by 0 days.

(21) Appl. No.: 15/524,959

(22) PCT Filed: Jan. 30, 2015

(86) PCT No.: PCT/CN2015/071958
§ 371 (c)(1),
(2) Date: May 5, 2017

(87) PCT Pub. No.: WO2016/070500
PCT Pub. Date: May 12, 2016

(65) Prior Publication Data
US 2017/0340776 A1 Nov. 30, 2017

(30) Foreign Application Priority Data

Nov. 6, 2014 (CN) .......................... 201410617017.1

(51) Int. Cl.
| | | |
|---|---|---|
| *A61L 27/46* | (2006.01) | |
| *A61L 27/32* | (2006.01) | |
| *A61L 27/50* | (2006.01) | |
| *A61B 17/88* | (2006.01) | |

(52) U.S. Cl.
CPC ............... *A61L 27/46* (2013.01); *A61L 27/32* (2013.01); *A61L 27/50* (2013.01); *A61B 17/88* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 2012/0191214 A1* | 7/2012 | Nies | ..................... | A61L 24/0084 |
| | | | | 623/23.62 |
| 2012/0330436 A1* | 12/2012 | Bohner | ................. | A61L 31/026 |
| | | | | 623/23.63 |

FOREIGN PATENT DOCUMENTS

| | | | |
|---|---|---|---|
| CN | 1192700 | * | 9/1998 |
| CN | 1865270 | * | 11/2006 |
| CN | 101342384 | * | 8/2008 |
| CN | 101342384 | * | 1/2009 |
| CN | 101342384 A | | 1/2009 |
| CN | 101560326 A | | 10/2009 |
| CN | 101716377 A | | 6/2010 |
| CN | 101342383 B | | 9/2011 |
| CN | 102580144 A | | 7/2012 |
| CN | 104307048 A | | 1/2015 |
| RU | 2278164 | * | 6/2006 |
| WO | 2003049780 A1 | | 6/2003 |

OTHER PUBLICATIONS

Li et al. "Degradable biocomposite of nano calcium-deficient hydroxyapatite-multi(amino acid) copolymer"2012.*
Natelson et al. "The Effect of Oral Administration of Calcium Fructose Diphosphate on the Serum Organic Phosphate, Inorganic Phosphate, Calcium, Protein, and Citric Acid Levels" 1951. abstract.*
Jones et al. "Bone and Brain A Review of Neural, Hormonal, and Muscoskeletal Connections" 2004. abstract.*

* cited by examiner

*Primary Examiner* — Danah Al-Awadi
(74) *Attorney, Agent, or Firm* — Novick, Kim & Lee, PLLC; Allen Xue

(57) ABSTRACT

The present invention relates to the controllable degradation, filling-type complex bone implant of multivariant amino acid polymer-organic calcium/phosphorus salts, as well as to the preparative method thereof. The complex bone implant is consisted of multivariant amino acid polymers and medically acceptable organic calcium/phosphorus salts, while the content of organic calcium/phosphorus salts is 20-90% based on the total mass of composite material; the multivariant amino acid polymer is polymerized by ε-aminocaproic acid and at least two other amino acids, in which the molar content of ε-aminocaproic acid is at least 50% of the total molar quantity of amino acid polymers, while the amounts of other amino acids are at least 0.5% of the total molar quantity of amino acid polymers.

2 Claims, No Drawings

ND METHOD OF MAKING THEREOF

COMPOSITE BONE IMPLANT MATERIAL AND METHOD OF MAKING THEREOF

TECHNICAL FIELD

The present invention relates to the controllable degradation, filling-type complex bone implant of multivariant amino acid polymer-organic calcium/phosphorus salts, used for the defect repair of bone tissue, as well as to the preparative method thereof.

BACKGROUND ART

Clinical studies on bone healing and computer simulation analysis indicate that the bone healing is a continuous process. In general, that process can be divided into three stages: the hematoma organization stage, the formation stage of primary callus, and the callus transformation stage, and the healing cycle need about three months, but the complete recovery of physiological function of bones or joints need half a year or longer. In addition, the healing cycle of bone is further influenced by age, physical condition, fracture site, whether or not infection, and therapeutic method and so on. Thus, as far as bone repair material, whether its degradation rate can match the healing cycle of physiological bone is the key determining whether this material has a value in clinical application.

The product used for the repair of bone tissue in clinic may have two types, i.e. the filling type and the supporting type. The filling bone repair material is mostly used for the filling implant after cut due to trauma, tumor, as well as tuberculosis and so on; the supporting bone repair material can provide basic needs for mechanical support, and be used as implant for bone defect repair caused by pathological changes in backbone, four limbs, head, etc or by external injury.

At present, the bone repair material widely used includes different types such as autogenous bone, allogenic bone, xenogeneic bone, and artificial bone material and so on. Amongst, for the problems such as limited sources, non-shaping, and biosafety, etc, the clinical application of natural bones including autogenous bone, allogenic bone, xenogeneic bone and so on is limited very much.

Except for natural bones, artificial synthetic material used in the repair of bone tissue in clinic includes inorganic materials such as calcium sulfate, calcium phosphate, bioglass and so on, as well as bone-filling materials of organic polymer.

Although degradable inorganic materials have excellent biological performances and can guide the growth of bone tissue, its strength is low, and its friability is high, while it is often found as coating form. Meanwhile, after implanted in body, it can also develop a weak acid environment, that is not good for the repair of bone tissue or can induce inflammatory reaction (such as calcium sulfate). On the other hand, some inorganic calcium salt materials have a poor solubility and a long degradation cycle, such as the degradation of highly active hydroxyapatite is very slow and can remain in body for more than 10 years, and so long degradation cycle is not beneficial for the growth of new bone; while some inorganic calcium salts with high solubility can not match the growth rate of natural bone due to rapid degradation, and easily form collapsing, such as the complete degradation time of calcium sulfate and amorphous calcium phosphate used for repairing bone defect is 45-72 days, their degradation rates are more than twice that of natural bone.

Organic polymers may include polymethyl methacrylate plastics (PMMA), polylactic acid (PLA), polyglycolic acid (PGA), polycaprolactone (PCL), and polyamide (PA), etc. These materials have designability, and the molecular chain moiety can be designed according to the target products, while the surface properties and the degradation properties of materials can both be correspondingly processed, that is convenient for the standard and large-scale production. But, the hydrophilicity of most high molecular polymers is poor, and their biocompatibility is low, such as PMMA, PCL, etc, while for the degradable polymers such as polylactic acid (PLA), polyglycolic acid (PGA), etc, because of noumenon degradation, their in vivo degradation rates can not be controlled and easily lead to the collapse of materials, and the degradation products are acidic and can bring about adverse effects such as irritation, inflammatory reaction, etc.

Recently, research on complex bone implant constituted by simulating bone tissue becomes the hotspots and the emphasis of bone repair materials, such as HA/PA (hydroxyapatite/polyamide) complex bone implant, HA/PLA (hydroxyapatite/polylactic acid) complex bone implant, and CS/PGA (polyglycolic acid) complex bone implant and so on. These materials not only hold the mechanical property and the strength of polymers, but also can have biological activity of calcium/phosphorous salts.

Although these complex bone implants have gained some success in mechanical properties of material, they are still not desirable enough such as the dispersity of inorganic calcium/phosphorus salts in polymers is not good, and the problems in degradation rate and degradation products are still not effectively solved. Thus, in the face of so huge demand in clinic, high active complex bone implant of controllable degradation is urgently needed, whose degradation rate matches the healing-repair cycle of bone tissue. Moreover, the degradation cycle may be freely regulated, to meet the different requirements in clinic, and the degradation product cannot cause adverse effects on organism such as irritation, etc., and can stimulate the proliferation and differentiation of bone cells and promote the bone healing process, thus achieve synergetic effects of bone repair.

CONTENT OF INVENTION

Aiming directly at above conditions, the present invention provides a controllable degradation, filling-type complex bone implant of multivariant amino acid polymer-organic calcium/phosphorus salts, and further provides the preparative method thereof. A controllable degradation, filling-type complex bone implant of multivariant amino acid polymer-organic calcium/phosphorus salts.

A controllable degradation and filling-type complex bone implant of multivariant amino acid polymer-organic calcium/phosphorus salts of the present invention is constituted by multivariant amino acid polymers and medically acceptable organic calcium/phosphorus salts, the content of organic calcium/phosphorus salts is 20-90% based on the total mass of composite material, and the ratio is preferably 40-70%; the multivariant amino acid polymer is polymerized by ε-aminocaproic acid and at least two other amino acids, and preferably by ε-aminocaproic acid and three other amino acids, in which the molar content of ε-aminocaproic acid is at least 50% of the total molar quantity of amino acid polymers, while the amounts of other amino acids are at least 0.5% of the total molar quantity of amino acid polymers.

For above complex bone implant of the present invention, said multivariant amino acid polymers formed by ε-aminocaproic acid and other amino acids can be prepared by referring to those reported/used ways including the patent publication number CN101342383A ("Polymer-type of tissue repair material and the preparative method") by the present applicants. Amongst, said other amino acids can be selected from the group of glycine, alanine, phenylalanine, tryptophan, arginine, serine, tyrosine, threonine, leucine, proline, hydroxyproline, lysine, and γ-aminobutyric acid and so on, in which preferable is weakly basic amino acids or neutral amino acids that can be accepted by human body or exist in human body. On the one hand, addition of these other amino acids, especially such as phenylalanine, proline, tryptophan, hydroxyproline and the like with rigid molecular group, can more reduce the regularity of poly-ε-aminocaproic acid molecular chain and improve the degradation rate, and can further provide certain mechanical strength to ultivariant amino acid polymers; on the other hand, the degradation products of multivariant amino acid copolymers are small molecular oligopeptides or amino acid monomers, without toxicity and irritation, and their biosafety is high. The degradation rate of polymer itself can be freely adjusted by changing the composition/ratio of amino acids, as well as the polymerization time and temperature, thus, having an influence on the degradation rate of whole complex bone implant.

For above complex bone implants, said medically acceptable organic calcium/phosphorous salts preferably use the mixture formed by mixing at least one calcium/phosphorus-containing salt including calcium glycerophosphate, fructose diphosphate dicalcium, and calcium inositol hexaphosphate, with one calcium salt without phosphorus including calcium citrate, calcium lactate, calcium laurate, calcium oleate, calcium palmitate, calcium salicylate, calcium stearate, calcium succinate, calcium acetate, calcium gluconate, calcium D-saccharate, calcium L-threonate, calcium ascorbate, calcium tartrate, and calcium glycerate, except for single-use of salts simultaneously containing calcium and phosphorus elements. The mixture has advantages that the total molar ratio of Ca/P elements in organic calcium/phosphorus salts can be easily close to (1.5-1.67)/1, the ratio of normal bone in human body.

Organic calcium salts not only have high solubility, but also pH values of most of their solutions are neutral, and cannot cause strong change of pH value in surrounding physiological environment. At the same time, organic calcium salts can enhance the bone calcium content, the bone density, and the bone strength, as well as can reverse the negative calcium balance. The passive absorptivity of calcium is proportional to its intake amount, and the more the intake, the more the absorption. The calcium entering plasma by passive diffusion of molecules is present in small molecular form, improving total calcium concentration in blood, that makes the ratio of small molecular calcium in total calcium increase, i.e. relatively elongating the metabolism time of calcium in plasma. Molecular calcium salts in blood have temperate ability of dissociating calcium ions, not only prolonging metabolic time, but also providing enough time for blood calcium and bone calcium to carry out the metabolism, and thus the biological availability is high. The organic calcium polybasic carboxylate, widely used in calcium-supplement foods or pharmaceuticals, especially such as calcium citrate, calcium tartrate, and calcium succinate, etc., can effectively supplement calcium source, and may reinforce nutritional absorption and utilization of muscle cells, moreover, there are multiple absorption pathways in vivo, water-insoluble sediment form can be produced by intrinsic cycle, to enrich skeleton calcium library and fill up skeleton calcium; long-chain organic calcium salts with fatty acid chains such as calcium stearate, calcium laurate, and calcium oleate, etc., can be acid hydrolyzed to different fatty acids and corresponding calcium salts, that may not only provide different unsaturated or saturated fatty acids, participating in the circulation of lipid metabolism and protein metabolism, and the solubility of calcium salt constituents is high, while their absorption and availability is also high. In addition, organic calcium salts with carbocyclic ring structure, commonly found in pharmaceuticals such as calcium gluconate, calcium D-saccharate, and calcium L-threonate, etc., are also calcium strengtheners and nutritional agent, buffers, hardening agents, chelating agents commonly used in food additives, and can decrease capillary permeability, increase density, maintain normal excitability of nerves and muscles, increase myocardial contractile force, while can contribute to the formation of sclerotin.

During the development and maturation process of bone, organic phosphorus salts not only involve in balance modulation of calcium and phosphorus, but also take part in metabolism of sugars, lipids, and amino acids, regulate acid-base balance, and play a role in composition of skeleton and teeth. Except for constituting biomembrane, organic phosphorus salts also get involved in recognition of cell membrane to proteins and in signal transduction (such as lecithin, cephalin, and phosphatidyl glycerol, etc). Compounds of organic phosphorous salification mainly include cyclic phosphates such as fructose diphosphate dicalcium, inositol hexaphosphate, and glucose monophosphate calcium, etc. These organic phosphates are mostly intermediate products in the process of glucose metabolism, and can act on cell membrane and increase the concentrations of energy-rich phosphate bond and adenosine triphosphate in cells, thus promote influx of potassium ion, recover quiescent condition of cells, increase the content of diphosphoglyceric acid in erythrocytes, suppress liberation of oxygen radicals and histamine, improve cell functions.

Research has proved that above organic calcium/phosphorus salts are non-toxic, with good biocompatibility, and widely get used in the pharmaceutical and food industries and the same. These salts may have an effect on supplementing the physiologic function of calcium/phosphorus after use. For many advantages of organic calcium/phosphorus salts, utilizing the difference in solubility of different organic calcium/phosphorus salts can freely regulate the degradation period of materials.

Bone is constituted by bone minerals, bone matrix, and osteocytes, etc. Bone minerals can increase hardness of bones, bone matrix determines shapes and toughness of bones, and osteocytes play a leading role in the metabolism of bones. In order to simulate organic/inorganic composition of natural bones, for complex bone implant mentioned above, said medically acceptable organic calcium/phosphorus salts was prepared by mixing organic calcium salts with or without phosphorous, and that can more conveniently realize the molar ratio of calcium/phosphorus elements is closer to that of normal bones in human body, i.e. (1.5-1.67)/1; while above multivariant amino acid polymers can possess chemical structure similar to bone matrix proteins in human body, and thus above complex bone implant of the present invention can have good biomechanical properties and compatibility, and are allowed to have higher bioactivity by organic calcium/phosphorus constituents. Based on the above, by changing the ratio of calcium/phosphorus salts in total amount of complex bone implant and/or the molar ratio of Ca/P elements in calcium/phosphorus salts, the purpose of regulating the degradation rate for complex bone implant can be realized. Experimental results show that when the content of organic calcium/phosphorus salts is 40-70% of total mass of complex bone implant, the implant may have more desirable degradation cycle and change of pH value, and the weight-loss in in vitro simulated body fluid can be controlled in 8-30 weeks, more consistent with the healing and repair cycle of natural bone in human body. After degradation, pH value of soaking solution is in 6.5-7.5 range, with a little effect on local physiological environment, cannot cause any irritant reaction, and have an advantage to the cell growth and the tissue repair.

For the preparation of the controllable degradation, filling-type complex bone implant of multivariant amino acid polymer-organic calcium/phosphorus salts, the basic procedures are as follows: under inactive gas protection, said organic calcium/phosphorus salts with an above ratio, as well as ε-aminocaproic acid and other amino acid constituents are mixed and dissolved in water, and after dehydration at 150-200° C., the mixture is warmed to 200-260° C. for carrying out the in situ polymerization, to obtain the controllable degradation, filling-type complex bone implant of multivariant amino acid polymer-organic calcium/phosphorus salts.

Based on above preparative method, for further preferable way, above in situ polymerization reaction is carried out by two stages, and more desirable effects can be achieved. After dehydration, the reaction mixture is firstly heated to 200-210° C., to allow reactants to have a 1-3 h preliminary polymerization at molten state, then the mixture is further heated to 210-260° C. and continually reacts for 0.5-5 h to finish the polymerization and obtain said complex bone implant.

Increasing reaction temperature and/or elongating reaction time can both enlarge the polymerization degree and the molecular weight of composite materials, and the degradation rate of products obtained also correspondingly reduced. On the contrary, the degradation rate of products can be accelerated. In addition, by changing and adjusting the ingredient ratio of ε-aminocaproic acid and other amino acid, not only the performances and the degradation cycle of multivariant amino acid polymer can be regulated, but also the change in pH value of degradation environment can be modulated.

Moreover, organic calcium/phosphorus salts containing crystal water can further generate porous surface from spontaneous foaming during processing, and in complex bone implant, the dissolution of organic calcium/phosphorus salts can also produce micropores, increase the surface area of complex bone implant, promote its degradation rate, facilitate the release of growth factor for bone defect healing, and benefit for the rapid repair of bone defect.

As for the filling-type bone implants, above bone implant of the present invention may further be pulverized to particles with a particle diameter of 0.3-5 mm or processed to bar material with a diameter of 5-8 mm or piece material of (10-50 mm)×(3-15 mm)×(3-10 mm) and other suitable forms, to be fit for different actual demand in clinic.

Referring to approved methods in YY/T 0474-2004 trade standards, above complex bone implant of the present invention (materials) is subjected to experiment on degradation rate by in vitro simulated body fluid soaking, and the soaking solution uses SBF. At each time point, the sample is taken out and dried to constant weight, followed by measuring mass-loss rate. Experimental results show the complete weight-loss of complex bone implant according to the present invention can be adjusted as appropriate in a wide range of 4-60 weeks, and can fully suit and meet the needs of bone repair in clinic. The quantitative and qualitative analysis of degradation products indicates that the products are mainly oligopeptides or small molecular amino acids, with a high biosafety. Moreover, as the continuous release of calcium/phosphorus ions in complex bone implant, the constant accumulation of calcium/phosphorus ions in soaking solution can stimulate proliferation and differentiation of bone cells and facilitate bone healing. By cell culture, it is found that during the process of cell culture, the complex bone implant of the present invention has significant effects on cell proliferation, compared with a single form of multivariant amino acid polymer and/or reported complex bone materials using inorganic calcium/phosphorus salts and multivariant amino acid polymers. Thus, above controllable degradation, filling-type complex bone implant of multivariant amino acid polymer-organic calcium/phosphorus salts according to the present invention is a kind of filling-type bone repair materials, with controlled degradation cycle and good activity of inducing osteogenesis.

Hereinafter, the above content of present invention can further be illustrated in detail, combined with examples. But it should not be understood that above subject scope of the present invention is only limited to the following examples. Without departing from above technical spirit of the present invention, various alternations and changes that can be made by common technical knowledge in the field and commonly-used means should all be within the scope of the present invention.

EXAMPLE 1

ε-Aminocaproic acid, alanine, lysine, proline, γ-aminobutyric acid, calcium citrate tetrahydrate, and calcium glycerophosphate were respectively taken out 86.5 g, 4.5 g, 3 g, 5 g, 25.7 g, 63.02 g, 103.94 g, and added to 500 ml three-necked bottle, then dissolved and mixed with 130 ml distilled water. Under nitrogen protection and under stirring, the mixture was warmed to 150° C.-200° C. for dehydration, and then continued heating to 200-210° C. for melting and 2 h prepolymerization, and then further heated to 220° C. and kept for 1 h. Under the protection of nitrogen, the reaction mixture was cooled to ambient temperature, to obtain 265 g complex bone implant materials of calcium citrate-calcium glycerophosphate/multivariant amino acid polymer. The obtained composite material was crushed to 2-5 mm complex bone implant of organic calcium/phosphorus salt-multivariant amino acid, and the content of calcium/phosphorus salts in complex bone implant was 60%, and Ca/P ratio was 1.67 by analysis.

The complex bone implant of calcium citrate-calcium glycerophosphate-multivariant amino acid was subjected to in vitro soaking test in simulated body fluid, and the culture experiment of L929 fibroblasts in extracting solution, using the composite material of calcium sulfate-calcium hydrogen phosphate-multivariant amino acid polymer as control, that was prepared with inorganic calcium/phosphorus salts by the same technology. After soaking for one week, the concentration of calcium ions in degradation solution of test sample was 3.2 times that of control sample, while the concentration of phosphorus ions was 2.4 times that of control sample. As for soaking in simulated body solution for 24 weeks, the weight-loss of experimental sample was 48% in the previous four weeks; the weight-loss was 65% in 12 weeks; the weight-loss was 88% in 24 weeks; pH values were remained in the range of 6.7-7.3 during the process of degradation. While, the weight-loss ratio of control sample was only 48% in 24 weeks, and the degradation cycle of control sample is relatively long using same technological conditions of preparation.

After L929 fibroblasts were cultured for 72 h with extracting solution of test sample according to the present invention, the cell proliferation rate was 124% calculated by MTT method, and the toxicity was 0 grade. While, the cell proliferation rate of control sample was only 106%, with a low cell activity.

EXAMPLE 2

ε-Aminocaproic acid, lysine, proline, γ-aminobutyric acid, calcium citrate tetrahydrate, and calcium glycerophosphate were respectively taken out 98.25 g, 3 g, 5 g, 21.7 g, 53.50 g, 118.24 g, and added to 500 ml three-necked bottle, then dissolved and mixed with 130 ml distilled water. Under nitrogen protection and under stirring, the mixture was warmed to 150° C.-200° C. for dehydration, and then continued heating to 210° C. for melting and 2 h prepolymerization, and then further heated to 220-230° C. and reacted for 1 h. Under the protection of nitrogen, the reaction mixture was cooled to ambient temperature, to obtain 275 g complex bone implant materials of calcium citrate-calcium glycerophosphate/multivariant amino acid polymer. The obtained composite material was crushed to 2-5 mm complex bone implant of organic calcium/phosphorus salt-multivariant amino acid, and the content of calcium/phosphorus salts in complex bone implant was 60%, and Ca/P ratio was 1.50 by analysis.

The complex bone implant of calcium citrate-calcium glycerophosphate-multivariant amino acid was subjected to in vitro soaking test in simulated body fluid, and the culture experiment of L929 fibroblasts in extracting solution, using the composite material of calcium phosphate-multivariant amino acid polymer as control, that was prepared by the same technology. After soaking for concentration one week, the of calcium ions in degradation solution of test sample was 6.9 times that of control sample, while the concentration of phosphorus ions was 4.7 times that of control sample. As for soaking in simulated body solution for 24 weeks, the weight-loss of experimental sample was 36% in the previous four weeks; the weight-loss was 58% in 12 weeks; the weight-loss was 73% in 24 weeks; pH values were remained in the range of 6.6-7.4 during the process of degradation. While, the weight-loss ratio of control sample was only 31% in 24 weeks, and the degradation cycle of control sample is too long under same technological conditions of preparation, that are not good for the bone ingrowth.

After L929 fibroblasts were cultured for 72 h with extracting solution of test sample according to the present invention, the cell proliferation rate was 120% calculated by MTT method, and the toxicity was 0 grade. While, the cell proliferation rate of control sample was only 101%, with a low cell activity.

EXAMPLE 3

ε-Aminocaproic acid, alanine, phenylalanine, lysine, proline, γ-aminobutyric acid, calcium citrate tetrahydrate, and calcium glycerophosphate were respectively taken out 86.5 g, 3 g, 7 g, 2 g, 4.6 g, 20.6 g, 58.55 g, 107.83 g, and added to 500 ml three-necked bottle, then dissolved and mixed with 130 ml distilled water. Under nitrogen protection and under stirring, the mixture was warmed to 150° C.-200° C. for dehydration, and then continued heating to 210±5° C. for melting and 2 h prepolymerization, and then further heated to 230±5° C. and reacted for 1 h. Under the protection of nitrogen, the reaction mixture was cooled to ambient temperature, to obtain 265 g complex bone implant materials of calcium citrate-calcium glycerophosphate/multivariant amino acid polymer. The obtained composite material was crushed to 2-5 mm complex bone implant of organic calcium/phosphorus salt-multivariant amino acid. The content of calcium/phosphorus salts in complex bone implant was 60%, and Ca/P ratio was 1.60 by analysis.

The complex bone implant of calcium citrate-calcium glycerophosphate-multivariant amino acid was subjected to in vitro soaking test in simulated body fluid, and the culture experiment of L929 fibroblasts in extracting solution, using the composite material of bone-like apatite-multivariant amino acid polymer as control, that was prepared by the same technology. After soaking for one week, the concentration of calcium ions in degradation solution of test sample was 5.3 times that of control sample, while the concentration of phosphorus ions was 2.5 times that of control sample. As for soaking in simulated body solution for 24 weeks, the weight-loss of experimental sample was 59% in the previous four weeks; the weight-loss was 87% in 12 weeks; the weight-loss was complete in 16 weeks; pH values were remained in the range of 6.5-7.2 during the process of degradation. While, the weight-loss ratio of control sample was only 26% in 24 weeks, and the degradation cycle of control sample is too long under same technological conditions of preparation, that are not good for the bone ingrowth.

After L929 fibroblasts were cultured for 72 h with extracting solution of test sample according to the present invention, the cell proliferation rate was 131% calculated by MTT method, and the toxicity was 0 grade. While, the cell proliferation rate of control sample was only 109%, with a low cell activity.

EXAMPLE 4

ε-Aminocaproic acid, glycine, alanine, phenylalanine, lysine, proline, calcium citrate tetrahydrate, and calcium glycerophosphate were respectively taken out 108 g, 3 g, 6 g, 7 g, 1 g, 6 g, 19.19 g, 31.66 g, and added to 250 ml three-necked bottle, then dissolved and mixed with 70 ml distilled water. Under nitrogen protection and under stirring, the mixture was warmed to 150° C.-200° C. for dehydration, and then continued heating to 210° C. for melting and 2 h prepolymerization, and then further heated to 220° C. and reacted for 1 h. Under the protection of nitrogen, the reaction mixture was cooled to ambient temperature, to obtain 161 g complex bone implant materials of calcium citrate-calcium glycerophosphate/multivariant amino acid polymer. The obtained composite material was crushed to 2-5 mm complex bone implant of organic calcium/phosphorus salt-multivariant amino acid. The content of calcium/phosphorus salts in complex bone implant was 30%, and Ca/P ratio was 1.67 by analysis.

The complex bone implant of organic calcium/phosphorus salt-multivariant amino acid was soaked in simulated body fluid for 24 weeks, the weight-loss of experimental sample was 19% in the previous four weeks; the weight-loss was 30% in 12 weeks; the weight-loss was 44% in 24 weeks; pH values were remained in the range of 6.8-7.5 during the process of degradation.

After L929 fibroblasts were cultured for 72 h with extracting solution of test sample according to the present invention, the cell proliferation rate was 118% calculated by MTT method, and the toxicity was 0 grade.

EXAMPLE 5

ε-Aminocaproic acid, alanine, phenylalanine, threonine, proline, hydroxyproline, calcium citrate tetrahydrate, and calcium glycerophosphate were respectively taken out 105 g, 1.7 g, 3 g, 1.5 g, 6.9 g, 10 g, 43.40 g, 71.57 g, and added to 500 ml three-necked bottle, then dissolved and mixed with 130 ml distilled water. Under nitrogen protection and under stirring, the mixture was warmed to 150° C.-200° C. for dehydration, and then continued heating to 210±5° C. for melting and 2 h prepolymerization, and then further heated to 230-240° C. and reacted for 1 h. Under the protection of nitrogen, the reaction mixture was cooled to ambient temperature, to obtain 219 g complex bone implant materials of calcium citrate-calcium glycerophosphate/multivariant amino acid polymer. The obtained composite material was crushed to 2-5 mm diameter of complex bone implant of organic calcium/phosphorus salt-multivariant amino acid. The content of calcium/phosphorus salts in complex bone implant was 50%, and Ca/P ratio was 1.67 by analysis.

The complex bone implant of organic calcium/phosphorus salt-multivariant amino acid was soaked in simulated body fluid for 24 weeks, the weight-loss was 39% in the previous four weeks; the weight-loss was 48% in 12 weeks; the weight-loss was 61% in 24 weeks; pH values were remained in the range of 6.7-7.4 during the process of degradation.

After L929 fibroblasts were cultured for 72 h with said extracting solution, the cell proliferation rate was 126% calculated by MTT method, and the toxicity was 0 grade.

EXAMPLE 6

ε-Aminocaproic acid, lysine, proline, γ-aminobutyric acid, calcium gluconate, and calcium glycerophosphate were respectively taken out 98.25 g, 3 g, 5 g, 21.27 g, 96.24 g, 67.26 g, and added to 500 ml three-necked bottle, then dissolved and mixed with 130 ml distilled water. Under nitrogen protection and under stirring, the mixture was gradually warmed to 150° C.-200° C. for dehydration, and then continued heating to 210° C. for melting and 2 h prepolymerization, and then further heated to 220±5° C. and reacted for 1 h. Under the protection of nitrogen, the reaction mixture was cooled to ambient temperature, to obtain 263 g complex bone implant materials of calcium gluconate-calcium glycerophosphate/multivariant amino acid polymer. The obtained composite material was crushed to 2-5 mm diameter of complex bone implant of organic calcium/phosphorus salt-multivariant amino acid. The content of calcium/phosphorus salts in complex bone implant was 60%, and Ca/P ratio was 1.67 by analysis.

The complex bone implant of organic calcium/phosphorus salt-multivariant amino acid was soaked in simulated body fluid for 24 weeks, the weight-loss was 63% in the previous four weeks; the weight-loss was 81% in 8 weeks; the weight-loss was complete in 11 weeks; pH values were remained in the range of 7.0-7.5 during the process of degradation.

After L929 fibroblasts were cultured for 72 h with the extracting solution of complex bone implant, the cell proliferation rate was 119% calculated by MTT method, and the toxicity was 0 grade.

EXAMPLE 7

ε-Aminocaproic acid, lysine, proline, γ-aminobutyric acid, calcium tartrate, and fructose diphosphate dicalcium were respectively taken out 98.25 g, 3 g, 5 g, 21.7 g, 38.35 g, 126.65 g, and added to 500 ml three-necked bottle, then dissolved and mixed with 130 ml distilled water. Under nitrogen protection and under stirring, the mixture was gradually warmed to 150° C.-200° C. for dehydration, and then continued heating to 210° C. for melting and 2 h prepolymerization, and then further heated to 220° C. and reacted for 1 h. Under the protection of nitrogen, the reaction mixture was cooled to ambient temperature, to obtain 269 g complex bone implant materials of calcium tartrate-fructose diphosphate dicalcium/multivariant amino acid. The obtained composite material was crushed to 2-5 mm diameter of complex bone implant of organic calcium/phosphorus salt-multivariant amino acid. The content of calcium/phosphorus salts in complex bone implant was 60%, and Ca/P ratio was 1.67 by analysis.

The complex bone implant of organic calcium/phosphorus salt-multivariant amino acid copolymer was soaked in simulated body fluid for 24 weeks, the weight-loss was 74% in the previous four weeks; the weight-loss was complete in 9 weeks; pH values were remained in the range of 6.7-7.1 during the process of degradation.

After L929 fibroblasts were cultured for 72 h with the extracting solution of complex bone implant, the cell proliferation rate was 114% calculated by MTT method, and the toxicity was 0 grade.

EXAMPLE 8

ε-Aminocaproic acid, lysine, proline, γ-aminobutyric acid, calcium citrate tetrahydrate, and calcium glycerophosphate were respectively taken out 95 g, 3 g, 5 g, 24 g, 68.80 g, 106.87 g, and added to 500 ml three-necked bottle, then dissolved and mixed with 130 ml distilled water. Under nitrogen protection and under stirring, the mixture was gradually warmed to 150° C.-200° C. for dehydration, and then continued heating to 210±5° C. for obtaining the melting state and for carrying out 3 h prepolymerization, and then further heated to 250° C. and reacted for 2 h. Under the protection of nitrogen, the reaction mixture was cooled to ambient temperature, to obtain 272 g complex bone implant materials of calcium citrate-calcium glycerophosphate/multivariant amino acid. The obtained composite material was crushed to 2-5 mm diameter of complex bone implant of organic calcium/phosphorus salt-multivariant amino acid. The content of calcium/phosphorus salts in complex bone implant was 60%, and Ca/P ratio was 1.67 by analysis.

The complex bone implant of organic calcium/phosphorus salt-multivariant amino acid copolymer was soaked in simulated body fluid for 24 weeks, the weight-loss was 20% in the previous four weeks; the weight-loss was 38% in 12 weeks; the weight-loss was 43% in 24 weeks; pH values were remained in the range of 6.7-7.3 during the process of degradation.

After L929 fibroblasts were cultured for 72 h with the extracting solution, the cell proliferation rate was 121% calculated by MTT method, and the toxicity was 0 grade.

EXAMPLE 9

ε-Aminocaproic acid, lysine, proline, γ-aminobutyric acid, calcium citrate tetrahydrate, and calcium glycerophosphate were respectively taken out 90 g, 3 g, 5 g, 28 g, 64.20 g, 105.89 g, and added to 500 ml three-necked bottle, then dissolved and mixed with 130 ml distilled water. Under nitrogen protection and under stirring, the mixture was gradually warmed to 150° C.-200° C. for dehydration, and then continued heating to 210° C. for obtaining the melting state, to carry out 1 h prepolymerization, and then further heated to 220±5° C. and reacted for 0.5 h. Under the protection of nitrogen, the reaction mixture was cooled to ambient temperature, to obtain 272 g complex bone implant materials of calcium citrate-calcium glycerophosphate/multivariant amino acid. The obtained composite material was crushed to 2-5 mm diameter of complex bone implant of organic calcium/phosphorus salt-multivariant amino acid. The content of calcium/phosphorus salts in complex bone implant was 60%, and Ca/P ratio was 1.67 by analysis.

The complex bone implant of organic calcium/phosphorus salt-multivariant amino acid copolymer was soaked in simulated body fluid for 24 weeks, the weight-loss was 78% in the previous four weeks; the weight-loss was complete in 9 weeks; pH values were remained in the range of 6.8-7.5 during the process of degradation.

After L929 fibroblasts were cultured for 72 h with the extracting solution, the cell proliferation rate was 127% calculated by MTT method, and the toxicity was 0 grade.

EXAMPLE 10

ε-Aminocaproic acid, lysine, proline, γ-aminobutyric acid, calcium citrate tetrahydrate, and calcium glycerophosphate were respectively taken out 95 g, 3 g, 5 g, 24 g, 28.80 g, 47.50 g, and added to 250 ml three-necked bottle, then dissolved and mixed with 70 ml distilled water. Under nitrogen protection and under stirring, the mixture was gradually warmed to 150° C.-200° C. for dehydration, and then continued heating to 210° C. for obtaining the melting state, to carry out 2 h prepolymerization, and then further heated to 220° C. and reacted for 1 h. Under the protection of nitrogen, the reaction mixture was cooled to ambient temperature, to obtain 182 g complex bone implant materials of calcium citrate-calcium glycerophosphate/multivariant amino acid. The materials were processed to bar of Φ6 mm×7 mm and piece of 10 mm×10 mm×5 mm. The content of calcium/phosphorus salts in complex bone implant of said two process specifications was 40%, and Ca/P ratio was 1.67 by analysis.

The complex bone implant of Φ6 mm×7 mmbar was soaked in simulated body fluid for 24 weeks, the weight-loss was 41% in the previous four weeks; the weight-loss was 63% in 12 weeks; the weight-loss was 73% in 24 weeks; pH values were remained in the range of 6.7-7.1 during the process of degradation.

The complex bone implant of 10 mm×10 mm×5 mm piece was soaked in simulated body fluid for 24 weeks, the weight-loss was 21% in the previous four weeks; the weight-loss was 37% in 12 weeks; the weight-loss was 54% in 24 weeks; pH values were remained in the range of 6.6-7.5 during the process of degradation.

After L929 fibroblasts were cultured for 72 h with the extracting solution of Φ6 mm×7 mm bar, the cell proliferation rate was 124% calculated by MTT method, and the toxicity was 0 grade. For the complex bone implant of 10 mm×10 mm×5 mm piece, the cell proliferation rate was 120%, and the toxicity was 0 grade.

COMPARATIVE EXAMPLE 1

Calcium sulphatedihydrate powder was processed to cylinder-shaped particles of Φ6 mm×5 mm, and after soaking in simulated body fluid for 5 weeks, the weight-loss was complete. pH values of soaking solution were remained in the range of 6.1-6.8. The degradation cycle was too fast, and calcium sulfate materials used for filling and repairing of bone easily collapsed, that are not good for growing and healing of bone tissue.

After L929 fibroblasts were cultured for 72 h with the extracting solution of calcium sulfate, the cell proliferation rate was 91% calculated by MTT method, and the toxicity was 1 grade. The cell proliferation rate was lower, because the degradation surroundings of calcium sulfate were acid, lacking synergistic effect of phosphorus element.

COMPARATIVE EXAMPLE 2

Calcium phosphate powder was processed to cylinder-shaped particles of Φ6 mm×5 mm, and after soaking in simulated body fluid for 24 weeks, the weight-loss was 3% in the previous four weeks; the weight-loss was 8% in 12 weeks; the weight-loss was 11% in 24 weeks; pH values were remained in the range of 7.2-7.5. The degradation cycle was too long, that are not good for growth of new bone.

The invention claimed is:

1. A bone implant composite, comprising:
   a multivariant amino acid polymer and a medically acceptable organic calcium/phosphorus salt, and a content of the organic calcium/phosphorus salt is 60% based on a total mass of the composite,
   wherein a molar ratio of calcium and phosphorus combined in said organic calcium/phosphorus salt is in a range of 1.5-1.67,
   wherein the medically acceptable organic calcium/phosphorus salt is calcium tartrate-fructose diphosphate dicalcium; and the multivariant amino acid polymer is polymerized by ε-aminocaproic acid, lysine, proline, and γ-aminobutyric acid, and
   wherein a molar content of ε-aminocaproic acid is at least 50% of a total molar quantity of the multivariant amino acid polymer and a molar content of lysine or proline is at least 0.5% of the total molar quantity of the multivariant amino acid polymer.

2. The bone implant composite according to claim 1, wherein the medically acceptable organic calcium/phosphorus salt is formed by mixing fructose diphosphate dicalcium and calcium tartrate.

* * * * *